(12) United States Patent
Georgieff (10) Patent No.: US 6,328,708 B1
(45) Date of Patent: Dec. 11, 2001

(54) DEVICE FOR CONTROLLED ANAESTHESIA, ANALGESIA AND /OR SEDATION

(76) Inventor: Michael Georgieff, Panoramastrasse 29, 89081 Ulm/Ermingen (DE)

( * ) Notice: Subject to any disclaimer, the term of this patent is extended or adjusted under 35 U.S.C. 154(b) by 0 days.

(21) Appl. No.: 09/037,793

(22) Filed: Mar. 10, 1998

(30) Foreign Application Priority Data

Mar. 10, 1997 (DE) .............................. 197 09 704
Aug. 8, 1997 (EP) ................................. 97113757

(51) Int. Cl.⁷ .................................................. A61M 37/00
(52) U.S. Cl. ............................................................ 604/26
(58) Field of Search ............................. 604/23, 24, 30, 604/31, 32, 33, 34, 80, 81, 246, 247, 248–250; 424/423; 514/816, 937

(56) References Cited

U.S. PATENT DOCUMENTS

| 4,622,219 | * | 11/1986 | Haynes . |
| 4,725,442 | | 2/1988 | Haynes . |
| 4,905,685 | * | 3/1990 | Olsson et al. . |
| 4,989,597 | * | 2/1991 | Werner . |
| 5,088,499 | * | 2/1992 | Unger . |
| 5,334,381 | | 8/1994 | Unger . |
| 5,585,112 | | 12/1996 | Unger et al. . |
| 5,653,998 | | 8/1997 | Hamann et al. . |
| 6,007,529 | * | 12/1999 | Gustafsson et al. . |
| 6,032,665 | * | 3/2000 | Psaros . |

FOREIGN PATENT DOCUMENTS

| 2937290 | | 4/1980 | (DE) . |
| 2513797 | | 7/1987 | (DE) . |
| 4132677 | | 4/1993 | (DE) . |
| 4432378 | | 3/1996 | (DE) . |
| 0 357 163 | * | 3/1990 | (EP) . |
| 0 370 637 | | 5/1990 | (EP) . |
| 0 523 315 | | 1/1993 | (EP) . |
| 85/00011 | | 1/1985 | (WO) . |
| 92/11052 | | 7/1992 | (WO) . |
| 95/27438 | | 10/1995 | (WO) . |
| 96/39197 | | 12/1996 | (WO) . |
| 96/41647 | * | 12/1996 | (WO) . |

OTHER PUBLICATIONS

Anesth Analg, 1996, 82, pp. 103–107, "A Pilot Study of the Effects of a Perflubron Emulsion, AF 0104, on Mixed Venour Oxygen Tension in Anesthetized Surgical Patients", Joyce A. Wahr, M.D. et al.

John C. Krantz, Jr. et al., "Current Comment: A Note on the Intarvenous Use of Anesthetic Emulsions in Animals and Man with Special Reference to Methoxyflurane" *Anesthesiology*, vol. 22, pp. 491–492 (1961).

(List continued on next page.)

Primary Examiner—Manuel Mendez
(74) Attorney, Agent, or Firm—Burns, Doane, Swecker & Mathis, L.L.P.

(57) ABSTRACT

A device for inducing anaesthesia, analgesia and/or sedation is described which comprises a container holding an inert gas-containing liquid preparation, allowing for the controlled administration of the preparation to a patient.

3 Claims, 3 Drawing Sheets

OTHER PUBLICATIONS

John C. Krantz, Jr. et al., "Anesthesia LXIV: The Intravenous Administration of Methoxyflurane (Penthrane) Emulsions in Animals and Man" *Anesth. Analg.*, vol. 41, pp.257–262 (1962).

Helmut F. Cascorbi, M.D., Ph.D., et al., "Hazards of Methoxyflurane Emulsions in Man", "Hazards of Methoxyflurane Emulsions in Man", *Anesth. Analg.* vol. 47, pp. 557–559 (1968).

Kadhim N. Salman, Ph.D., et al, "Intravenous Administration of a New Volatile Anesthetic, 2,2–Dichloro–1,1–Diflurooethyl Methyl Sulfide, in Dogs and Monkeys", "Intravenous Administration of a New Volatile Anesthetic...", *A. J. Vet. Res.* vol. 29, pp. 165–172 91968).

Pschyrembel, Klinisches Worterbuch, Walter de Gruyter, Berlin–New York 1977, p. 48.

B. Biber et al., "Intravenous infusion of halothane dissolved in fat. Haemodynamic effects in dogs," Acta Anaesthesiol Scand 1984, 28, p. 385–389.

B. Lachmann et al., "Safety and efficacy of xenon in routine use of an inhalational anaesthetic", The Lancet, vol. 335 (Jun. 16, 1990), p. 1413–1415.

H. Luttropp et al., "Left ventricular performance and cerebral haemodynamics during xenon anaesthesia", Anaesthesia, 1993, vol. 48, p. 1045–1049.

F. Giunta et al., "Xenon: a review of its anaesthetic and pharmacological properties", Applied Cardiopulmonary Pathophysiology 00: 1–9, 1996.

Ullmanns Encyklopädie der technischen Chemie, 4. ed., vol. 17, Chapter 'Narkosemittel, Verlag Chemie, WeinheimNew York 1979; p. 135–141.

S. Schraag und M. Georgieff, "Intravenös Anasthesis–Aktuelle Aspekte", Anasthesiol Intensivmed. Notfallmed. Schmerzther. 1995; 30:469–478; Georg Theieme Verlag Stuttgart–New York.

Rompp Chemie Lexikon (paperback–edition), vol. 5, Georg Theieme Verlag, Stuttgart 1995, "Propofol", p. 3639–3640.

J. Chem. Phys. 90 (11), Jun. 1, 1989, "Solubility on xenon in 45 oarganic solvents including cycloalkanes, acids, and alkanals: Experiment and theory", Gerald L. Pollack et al.*

Der Spiegel 15/1996, pp. 196–198, "Abstieg ins Undewusste".*

* cited by examiner

DEVICE FOR CONTROLLED ANAESTHESIA, ANALGESIA AND /OR SEDATION

The invention relates to a device which can be used to control the anaesthesia, analgesia and/or sedation of a patient.

Control is understood here as meaning that a patient's condition (anaesthesia, analgesia and/or sedation) can be changed in the shortest possible time from the patient's actual condition to a required or desired condition. This means e.g. that, in the case of anaesthesia, the conditions (1) analgesia, (2) loss of consciousness and (3) muscular relaxation are reached in the shortest possible time and that the transition from the anaesthetized condition to full consciousness proceeds rapidly and without complications. Control also means that, once a condition has been reached, it is kept stable over long periods (hours to days). This means that, even under drastically changing circumstances, the condition is maintained and subsequent control can be effected without problems.

If such control is to take place reliably and without complications, the active substance must first meet certain requirements. For example, one feature of the active substance must be a rapid onset of action (a few seconds). On the other hand, however, the action must also wear of f rapidly (for example 1–3 minutes; reversibility; all defunctionalization symptoms must disappear when anaesthesia has ended). A further requirement is an adequate (for example anaesthesio-logical) safety margin. The concentration required to achieve the desired condition (for example loss of pain sensation and loss of consciousness) should be several times lower than that which damages the patient's vital functions. Finally, however, the controllability is also a decisive factor, i.e. the condition can be deepened, relieved or ended by varying the concentration or the infusion rate. In the case of longer-lasting operations (e.g. operations which take more than 10 seconds), an additional requirement is that the active substance can be administered in higher concentrations over a longer period of time without causing appreciable side effects.

Although one of the remarkable features of the intravenous anaesthetics in current use is an immediate onset of action, they regularly exhibit a host of disadvantages. It should be emphasized that propofol and etomidate, in particular, have no analgesic action and are difficult to control. Other disadvantages of these injectable anaesthetics are side effects which are difficult to assess (for example drop in blood pressure, bradycardia, rigidity, allergic reactions) and in some cases serious contraindications. Finally, total intravenous anaesthesia (TIVA) with propofol also frequently results in protracted waking and disorientation, especially after longer periods of anaesthesia.

Thus it is seen that the presently known intravenous active substances do not meet the requirements.

Active substance combinations according to the state of the art do not represent a solution to this problem. In the case of anaesthetics in particular, it is known that combinations produce pharmacokinetic and pharmacodynamic interactions which very definitely cannot be adequately controlled in the maintenance of the anaesthesia. As a consequence of the different pharmacokinetics and pharmacodynamics of the respective active substances at a given moment during the anaesthesia, it is not possible correctly to adjust the concentration and/or the infusion rate. In other words, where active substance combinations are used in an intravenous preparation, the overall action virtually never corresponds to the sum of the individual actions. Such combination preparations therefore fail to meet the requirement of controllability.

There is consequently a need for a substance, to be used as a single substance or in combination with other active substances, which meets the requirements formulated above.

Very precise control of anaesthesia, especially the maintenance of anaesthesia, requires that a particular concentration of active substance in a patient's blood be unambiguously measurable at any time. In the case of simple and easily comprehensible operating procedures and known pharmacokinetics, limited control is possible by means of multistage infusion regimes, for example with propofol. However, such regimes are inflexible and are unsuitable especially when the active substance has to be administered in a controlled manner under changing anaesthetic and operative circumstances.

Because of the lack of flexibility of manual infusion regimes and the highly complex mathematical models for the pharmacokinetics of the known active substances, computer controlled infusion systems have been developed. These computer systems are programmed with a mathematical solution for the pharmacokinetic model of a patient in respect of the active substance used, for example propofol. The computer then calculates the infusion rate which is necessary to achieve and maintain a theoretical target blood concentration. This target value is determined and adjusted e.g. by an anaesthetist. The computer then also controls the infusion rate at which the active substance is administered to a patient. This type of control is also known as target controlled infusion (TCI).

However, there is always uncertainty as regards the concentration of the active substance because the pharmacokinetics differ from patient to patient. It has in fact been observed that very different target concentrations have been determined by anaesthetists in practice. It follows from this that there is a considerable need for a system which can adjust or control a particular condition during anaesthesia as a function of a patient's actual requirements during an operation. The substantial differences in the target concentrations of the active substance in the blood, and the appreciable variance observed in the course of operations with different patients and the drugs additionally used, lead to the conclusion that TCI does not yet meet the requirements of effective control in every respect.

Systems are currently under development which make it possible to adjust the degree of anaesthesia more precisely. These are closed circuit systems in which the administration of the injectable anaesthetic is controlled as a function of the depth of anaesthesia which is actually measured (so-called closed loop anaesthesia systems (CLAN)). However, these systems require a considerable expenditure on equipment in order precisely to determine the action of the anaesthetic, i.e. the depth of the anaesthesia, in a patient.

In summary, there is therefore not only a need for a substance with an anaesthetic, analgesic and sedative action which meets all the requirements for use in a true control system (TCI or CLAN), as previously discussed, but also a need for simpler systems which can also function without complex computer programs and/or expensive measuring instruments (as well as evaluation programs) and which, in contrast to the known systems, reflect the true condition (for example true concentration in the blood).

The object of the invention consists in providing a device (or facility) which makes it possible to ensure controlled anaesthesia, analgesia and/or sedation.

This object is achieved by means of a device which is characterized in that it comprises a container holding a liquid preparation which contains a lipophilic inert gas in an amount effective as an anaesthetic, analgesic or sedative, and means for the controlled administration of the preparation to the patient. The purpose of this device is to administer an inert gas-containing preparation to a patient intravenously or arterially in a time controlled manner. "In a time controlled manner" means here that the condition required for example in an operative procedure (anaesthesia, analgesia and/or sedation) can always be precisely controlled over a given period of time, for example 2 minutes or even 1 to 2 hours or more (up to days). This is achieved for example by aiming for a particular endtidal xenon concentration, which corresponds to the concentration in the blood. In the very simplest case, the container holding the liquid preparation is a syringe. The means of controlled administration is then the syringe plunger, to which a pressure is applied, for example with the assistance of a so-called perfuser, said pressure affording a controlled administration of the preparation (e.g. continuous intravenous administration of a volume of 20 ml over 30 sec). Such a device makes it possible to ensure the maintenance of anaesthesia over shorter periods of time (10 sec to about 60 min). The depth of anaesthesia, the analgesia, the sedation and/or the muscular relaxation is precisely adjusted for example via the endtidal xenon concentration. As the pharmacokinetics of the active substance are very much simpler than in the case of propofol, graded infusion regimes are not necessary.

Another embodiment comprises an infusion bag filled with the liquid preparation, a tube for connection to the patient, and a simple regulator for controlling the administration. More complex embodiments comprise electronic control facilities and pumps, for example infusion pumps.

The required adjustments for the infusion of the liquid preparation containing an inert gas can be determined inter alia by simulating the course of an operation on a patient beforehand, for example. This means that the infusion rate/concentration appropriate for a particular condition (anaesthesia/analgesia/ sedation) is determined on a patient beforehand. Such a determination can be carried out without problems immediately before the actual operation.

The invention is partly based on the surprising discovery that a condition of anaesthesia, analgesia or sedation can easily be controlled with a liquid preparation containing an inert gas (Kr, Ar, Xe). Xenon has proved particularly effective in this context.

Xenon is a colourless, odourless and tasteless monoatomic inert gas of atomic number 54. Xenon is five times denser than air. Naturally occurring xenon also contains isotopes, for example the isotopes 124, 126, 128, 129, 130, 131, 132, 134 and 136. Synthetic isotopes, like xenon 114, xenon 133 and xenon 142, are known as well. These isotopes disintegrate with half-lives of between 1.2 seconds and about 40 days. The present invention does not address radioactive xenon isotopes.

Liquid preparations in terms of the present invention are generally preparations which, by virtue of a certain lipophilicity, can easily take up a fat-soluble gas like the abovementioned xenon or krypton, examples of said preparations being emulsions.

To achieve a subanaesthetic action, the xenon load in the medicinal preparation need only be about 0.2 to 0.3 ml of xenon per ml of emulsion. This means that an analgesic and/or sedative action is assured for preparations with a xenon content of at least 0.2 ml/ml emulsion. An anti-inflammatory action is already observed at 0.1 ml/ml emulsion. It has been found that, with continuous infusion over 30 sec, 20 ml of an emulsion containing 0.3 ml of Xe per ml of emulsion produce a subanaesthetic condition in a patient weighing about 85 kg. When working with a highly laden perfluorocarbon emulsion containing 2 to 4 ml of xenon per ml of emulsion, for example, 20 ml of this emulsion are infused over 30 sec, for example, in order to induce anaesthesia. An infusion rate of at least 7.5 ml/min is sufficient to maintain the anaesthesia. A total of 470 ml of emulsion would thus be used for a 1-hour operation. With a xenon content of 3 ml of xenon per ml of emulsion, this corresponds to a xenon volume of 1410 ml, i.e. a fraction of the xenon consumed in inhalation anaesthesia (based on a body weight of 85 kg, this would be a consumption of 16.6 ml per kg in one hour).

It is furthermore possible, and under certain circumstances also advantageous, to include another pharmacologically active agent in the preparation in addition to the inert gas. This can be an intravenous sedative or anaesthetic, for example. Depending on whether this agent is water-soluble or fat-soluble, it is then present in the aqueous phase or the lipid phase together with the xenon. 2,6-Diisopropylphenol, which is an effective anaesthetic (for example 1.5–20 mg/ml), is found to be particularly suitable for this purpose. Etomidate in concentrations of 0.1–2 mg/ml (Hypnomidate®, an imidazole-5-carboxylic acid derivative) is also suitable. Using dissolved xenon in addition to the other anaesthetic makes it possible to lower the concentration of e.g. diisopropylphenol or etomidate which is necessary for anaesthetization. Thus, for example, 1 ml of fatty emulsion according to the invention (containing about 0.1 g of fat per ml of emulsion) can contain 2.5–20 mg of 2,6-diisopropyl-phenol, i.e. for example 2.5, 5.0, 7.5, 10, 15 or 20 mg, in addition to the xenon.

In very general terms, the substance with an anaesthetic, analgesic or sedative action which is present together with the xenon can be another anaesthetic, an analgesic, a muscle relaxant or a sedative. Examples of other suitable anaesthetics are barbiturates (barbital, phenobarbital, pentobarbital, secobarbital, hexobarbital and thiopental, inter alia) in general, and opioids. Known analgesics are, inter alia, compounds of the morphine type, e.g. hydromorphone, oxymorphone, codeine, hydrocodone, thebacon, thebaine and heroin. It is also possible to use synthetic derivatives of morphine, e. g. pethidine, levomethadone, dextromoramide, pentazocine, fentanyl and alfentanil. It is also possible to use less potent analgesics such as anthranilic acid derivatives (flufenamic acid, mefenamic acid), acrylic acid derivatives (diclofenac, tolmetin, zomepirac), arylpropionic acid derivatives (ibuprofen, naproxen, phenoprofen, ketoprofen) and indoleacetic or indenacetic acid derivatives (indometacin, sulindac). The muscle relaxants used can be central muscle relaxants, for example baclofen, carisoprodol, chlordiazepoxide, chlormezanone, chloroxazone, dantrolene, diazepam, phenyramidol, meprobamate, phenprobamate and orphenadrine. Sedatives which can be used according to the invention are, inter alia, benzodiazepine derivatives such as triazolam, lormetazeban, clotiazepam, flurazepam, nitrazepam and flunitrazepam.

Liquids which can take up lipophilic inert gases are e.g. blood substitutes, including perfluorocarbon emulsions (e.g. Perflubron).

It is generally known that a large number of gases have a high solubility in perfluorocarbon compounds. A perfluorocarbon emulsion consists for example of up to 90% (weight/volume) of perflubron ($C_8F_{17}$). Emulsifiers, for example phospholipids from chicken egg yolk, are additionally required. These emulsions which can be loaded according to the invention with xenon have been reported for example by J. A. Wahr et al. in Anesth. Analg. 1996, 82, 103–7.

Suitable fluorocarbon emulsions preferably comprise 20% w/v to 125% w/v of a highly fluorinated hydrocarbon compound, for example polyfluorinated bisalkylethenes, cyclic fluorocarbon compounds like fluorodecalin or perfluorodecalin, fluorinated adamantane, or perfluorinated amines like fluorinated tripropylamine and fluorinated tributylamine. It is also possible to use monobrominated perfluorocarbons, for example 1-bromoheptadecafluorooctane ($C_8F_{17}Br$), 1-bromopentadecafluoroheptane ($C_7F_{15}Br$) and 1-bromotridecafluorohexane ($C_6F^{13}Br$). Other compounds can also be used, including perfluoroalkylated ethers or polyethers, e.g. $(CF_3)_2CFO(CF_2CF_2)_2OCF(CF_3)_2$, $(CF_3)_2CFO-(CF_2CF_2)_3OCF_2(CF_3)$, $(CF_3)_2CFO(CF_2CF_2)_2F$, $(CF_3)_2CFO(CF_2CF_2)_3F$ and $(C_6F_{13})_2O$.

Chlorinated derivatives of the abovementioned perfluorocarbons can also be used.

The loading capacity of the abovementioned perfluorocarbon preparation is considerable. Xenon loads of e.g. 1 to 10 ml/ml have been achieved by the simplest means. For example, these preparations can be loaded with inert gas simply by having the gas passed through them.

It is also possible to use fatty emulsions containing the lipophilic inert gas dissolved or dispersed in the lipid phase.

It has been found that xenon can be added to a fatty emulsion in appreciable amounts. Thus, even by the simplest means, xenon can be dissolved or dispersed in concentrations of 0.2 to 10 ml or more per ml of fatty emulsion (concentrations relate to standard conditions, i.e. 20° C. and normal pressure). The xenon concentration depends on a large number of factors, especially the concentration of the fat. As a rule the preparations will be "loaded" with xenon up to the saturation limit. However, it is also possible for very small concentrations to be present, provided, for example, that a pharmacological activity can still be observed on intravenous administration. In the case of a 10% fatty emulsion, it is easily possible to reach xenon concentrations of 0.3 to 2 ml of xenon per ml of fatty emulsion. It is of course also possible to reach higher values, e.g. 3, 4, 5, 6 or 7 ml of xenon per ml of fatty emulsion. These fatty emulsions are sufficiently stable, at least in gas-tight containers, for the xenon not to be released as a gas over conventional storage periods.

The lipid phase of the preparation, which takes up the gas, i.e. which can dissolve and/or disperse their gas, is formed mainly of so-called fats, said fats being essentially esters of long-chain and medium-chain fatty acids. Such fatty acids, saturated or unsaturated, contain 8 to 20 carbon atoms. However, it is also possible to use omega-3 or omega-6 fatty acids, which can contain up to 30 carbon atoms. Suitable esterified fatty acids are especially plant oils, e.g. cottonseed oil, soya bean oil and thistle oil, fish oil and the like. The major constituent of these naturally occurring oils are fatty acid triglycerides. Preparations in the form of so-called oil-in-water emulsions are of particular importance, the proportion of fat in the emulsion conventionally being 5 to 30% by weight, preferably 10 to 20% by weight. As a rule, however, an emulsifier is present together with the fat, proven emulsifiers being soya phosphatides, gelatin or egg phosphatide. Such emulsions can be prepared by emulsifying the water-immiscible oil with water in the presence of the emulsifier, which is normally a surface-active agent. Other polar solvents can also be present with the water, examples being ethanol and glycerol (propylene glycol, hexylene glycol, polyethylene glycol, glycol monoethers, a water-miscible ester, etc.). The inert gas can already have been incorporated into the lipid phase in a previous process step. In the simplest case, however, the prepared emulsion is loaded with the xenon. This can take place at various temperatures, for example at temperatures from 1° C. to room temperature. It is occasionally useful here to apply a pressure, for example of up to 8 atmospheres or more, to the vessel containing the emulsion.

According to the invention, it is possible to use fatty emulsions such as those employed in intravenous feeding. These fatty emulsions consist essentially of a suitable fatty base (soya bean oil or sunflower seed oil) and a well-tolerated emulsifier (phosphatides). Fatty emulsions in general use are Intralipid®, Intrafate®, Lipofundin® S and Liposyn®. More detailed information on these fatty emulsions can be found in G. Kleinberger and H. Pamperl, Infusionstherapie, 108–117 (1983) 3. The fatty emulsions generally also contain additives which make the osmolarity of the aqueous phase, surrounding the fatty phase present in the form of liposomes, isotonic with the blood. Glycerol and/or xylitol can be used for this purpose. Furthermore, it is frequently useful to add an antioxidant to the fatty emulsion in order to prevent oxidation of the unsaturated fatty acids. Vitamin E (DL-tocopherol), in particular, is suitable for this purpose.

So-called liposomes, which can be formed from the abovementioned triglycerides but also generally from so-called phospholipid molecules, are particularly advantageous as the lipid phase, especially in the case of an oil-in-water emulsion. These phospholipid molecules generally consist of a water-soluble part, which is formed of at least one phosphate group, and a lipid part, which is derived from a fatty acid or fatty acid ester.

U.S. Pat. No. 5 334 381 illustrates in detail how liposomes can be loaded with gas. In very general terms, a device is filled with the liposomes, i.e. with an oil-in-water emulsion, and the device is then pressurized with the gas inside. The temperature can be reduced to as low as 1° C. in this process. The gas gradually dissolves under pressure and passes into the liposomes. Small gas bubbles may then form when the pressure is released, but these are now encapsulated by the liposomes. It is thus possible in practice to keep xenon gas or other gases, for example, in a fatty emulsion under hyperbaric conditions. Such preparations can also be used according to the invention, provided that a separate gas phase does not form outside the liposomes and on condition that the desired pharmacological action takes place.

The lipids which form the liposomes can be of natural or synthetic origin. Examples of such materials are cholesterol, phosphatidylcholine, phosphatidylethanolamine, phosphatidylserine, phosphatidylglycerol, phosphatidylinositol, sphingomyelin, glycosphingolipids, glucolipids, glycolipids, etc. The surface of the liposomes can moreover be modified by a polymer, for example by polyethylene glycol.

It is self-evident that the control device according to the invention can also include the determination of other experimental values on a patient (for example acoustically induced potentials etc.) in order to be able to monitor the desired controlled condition more precisely. As inert gases are only eliminated through ventilation via the lung, however, this is the first time that it has been possible, in the intravenous administration of the inert gas-containing preparation, continuously to determine the actual concentration of an intravenous drug by measurement of the endtidal concentration of the inert gas (particularly xenon). Therefore both the depth of anaesthesia and the depth of analgesia, as well as the muscular relaxation, if desired, can be precisely controlled by controlling various true arterial concentrations.

The invention thus affords real target controlled anaesthesia. No mathematical models for the effective plasma concentration are necessary in this case.

As elimination takes place exclusively via the lung, precise control of the anaesthesia is even possible in patients with a restricted organic function, for example a liver and/or kidney dysfunction.

The invention also provides a device for controlling anaesthesia, the intravenous supply of the inert gas-containing infusion solution being adjusted as a function of the inert gas concentration in the air exhaled by the patient.

The inert gas concentration in the exhaled air can be measured particularly easily, especially in the case of xenon, with a gas detector.

A characteristic feature of this device is that it is particularly simple in equipment terms. It can be used especially in emergency medicine, where facilities with a small space requirement are particularly advantageous.

This device can also be part of a unit used for monitoring/controlling anaesthesia with a gaseous anaesthetic.

The invention also provides a device for inducing sedation, especially analgesia/sedation, with (a) a facility which provides an emulsion containing a lipophilic inert gas in an amount active as a sedative, (b) a means of measuring data, which records a patient's data, said data allowing a conclusion to be drawn about the patient's condition, and (c) a control means which controls the administration of the emulsion from the facility to the patient as a function of the measured data. A device for (monitored) analgesia/sedation can be useful especially in the context of intensive care and after heart operations. This device comprises a perfuser, optionally a means of measuring the exhaled xenon, and a pulsoximeter. It is advantageous that analgesia can be achieved at the same time as sedation.

In summary, the device according to the invention can be used in a variety of circumstances, especially in intensive care, endoscopy, cystoscopy, superficial interventions and heart operations.

The invention also provides a device for controlled anaesthesia, the concentration of the xenon in a preparation administered intravenously to a patient being regulated as a function of the xenon concentration in the air exhaled by an anaesthetized patient. Such a device optionally has a mixer in which the preparation is mixed with the xenon. This mixer can be temperature controlled (range from 1° C. to 35° C.). (The preparation can also have been loaded with xenon beforehand.) As already described previously, the xenon dissolves substantially in this process. In the simplest case, the mixer can consist of a vessel through which the preparation is passed and which is partially surrounded by a semipermeable membrane permeable to xenon. The concentration of the xenon in the preparation is then essentially determined by the xenon pressure on the semipermeable membrane. Other auxiliary means, for example active or passive stirrer elements, can additionally be considered here in order to improve the dissolution and/or dispersion of the xenon gas. The dissolution or dispersion of the xenon can also be improved by ultrasonic irradiation. By simple observation of the patient, it is now possible easily to determine, during full anaesthesia, that xenon concentration in the exhaled air at which the anaesthesia is still adequate. If the depth of anaesthesia is below the adequate level, the latter can be attained by increasing the administration of xenon by means of the preparation. The supply of xenon via the preparation can now be controlled by the xenon load and the infusion rate (e.g. by means of conventional infusion pumps). This procedure virtually allows fine control of the anaesthesia, which could not be achieved hitherto with intravenous anaesthetics.

The invention also provides a device which substantially corresponds to the device described above except that there is no provision for the admixing of xenon. In such a case, the preparation is always already loaded with xenon and the anaesthesia is controlled by adjusting the infusion rate or the concentration of the xenon as a function of the measured expiratory xenon concentration. The concentration of xenon in the preparation can be reduced for example by admixing another preparation which does not contain inert gas. Here again, simple infusion pumps (optionally peristaltic pumps) serve the purpose according to the invention. Provision can be made for temperature control both in this device and in the previously described device where xenon is mixed in the preparation.

Figure 1:
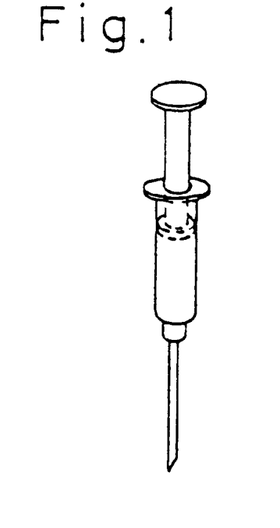
FIG. 1 shows a syringe such as that which can be used in principle according to the invention. In this very simple embodiment of the invention, the syringe, which holds a xenon-containing preparation, can be thought of as a facility providing a preparation which contains a lipophilic inert gas in an amount effective as an anaesthetic, analgesic or sedative.
Figure 2:
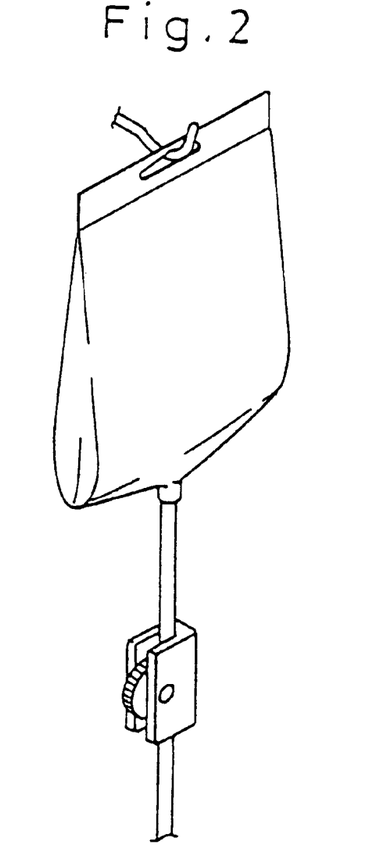
FIG. 2 shows a device according to the invention which is a filled infusion bag with a regulator.
Figure 3:
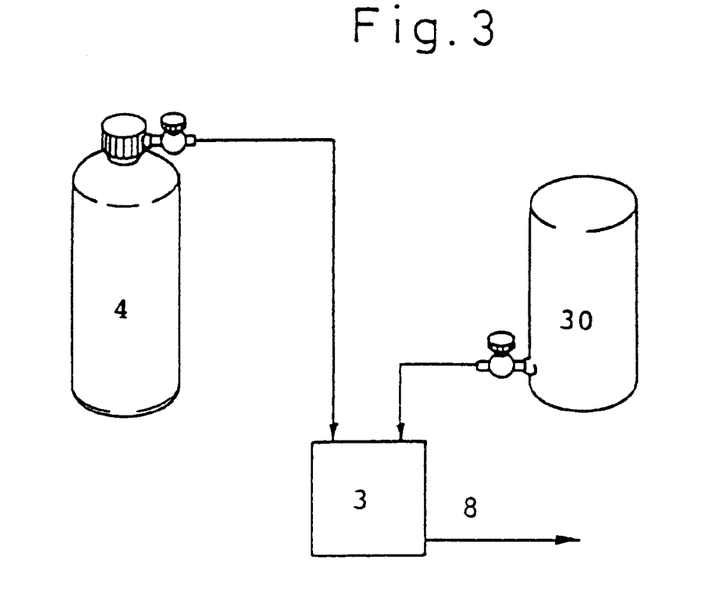
FIG. 3 shows a device according to the invention which has a filled infusion bag with a discharge tube, and a simple regulator for controlling the administration.

The device according to the invention for carrying out controlled anaesthesia is illustrated in greater detail with the aid of the diagram in FIG. 3.

This device comprises a storage container 30 for a liquid preparation capable of taking up an inert gas in dissolved form, a gas container 4 for the inert gas, and a mixer 3, in which the preparation is mixed with the inert gas. Control devices (infusion pumps, regulator etc.), with which the intravenous administration to the patient is controlled, are not shown.

Figure 4:
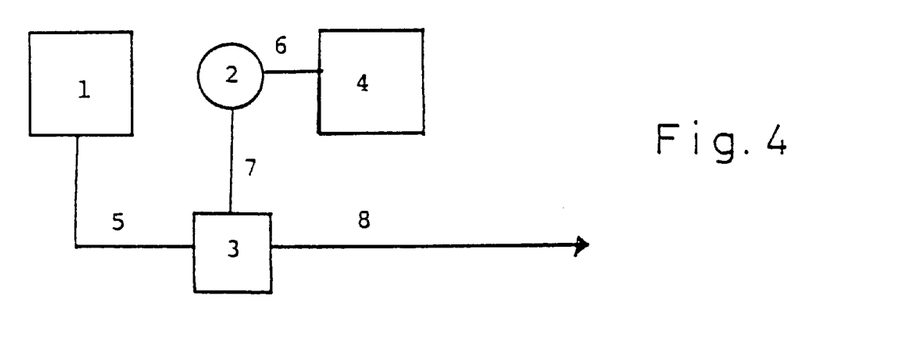
FIG. 4 another device according to the invention.

A device according to the invention is also illustrated in greater detail with the aid of the diagram in FIG. 4. This device can be used for controlled anaesthesia, the xenon concentration in the air exhaled by an anaesthetized patient being measured by analysis and the xenon concentration in a preparation administered intravenously to the patient being adjusted as a function of this analytical value. The device therefore comprises an optionally temperature-controllable storage container 1 (temperature range 1° C. to 35° C.) for the preparation, which is connected via a line 5 to a mixer 3, again optionally temperature-controllable. The xenon, which passes from a xenon bottle 4 into the mixer 3 via the line 6, the metering unit 2 and another line 7, is mixed with the preparation in the mixer 3, the bulk of the xenon dissolving in the emulsion. The xenon-containing preparation then passes via the line 8 and a venous access into a patient to be anaesthetized. The preparation is conveyed by means of pumps known per se (not shown). In the medical sector, so-called peristaltic pumps are used in the simplest case here. In the device according to the invention, such pumps can be provided for example in the line 5 and additionally in the line 8. The means of endexpiratoric gas sensory analysis, and the sampling means, are not shown. Conventionally the exhaled gas is sampled at the tube attachment or in the region of the mouth in the case of mask respiration or mask oxygenation during the patient's inhalation and exhalation. Methods of determining the xenon concentration in the exhaled air are generally known (gas detectors and the like).

(Various valves capable of regulating the inflow and outflow of solutions and gases are also not shown.)

Figure 5:
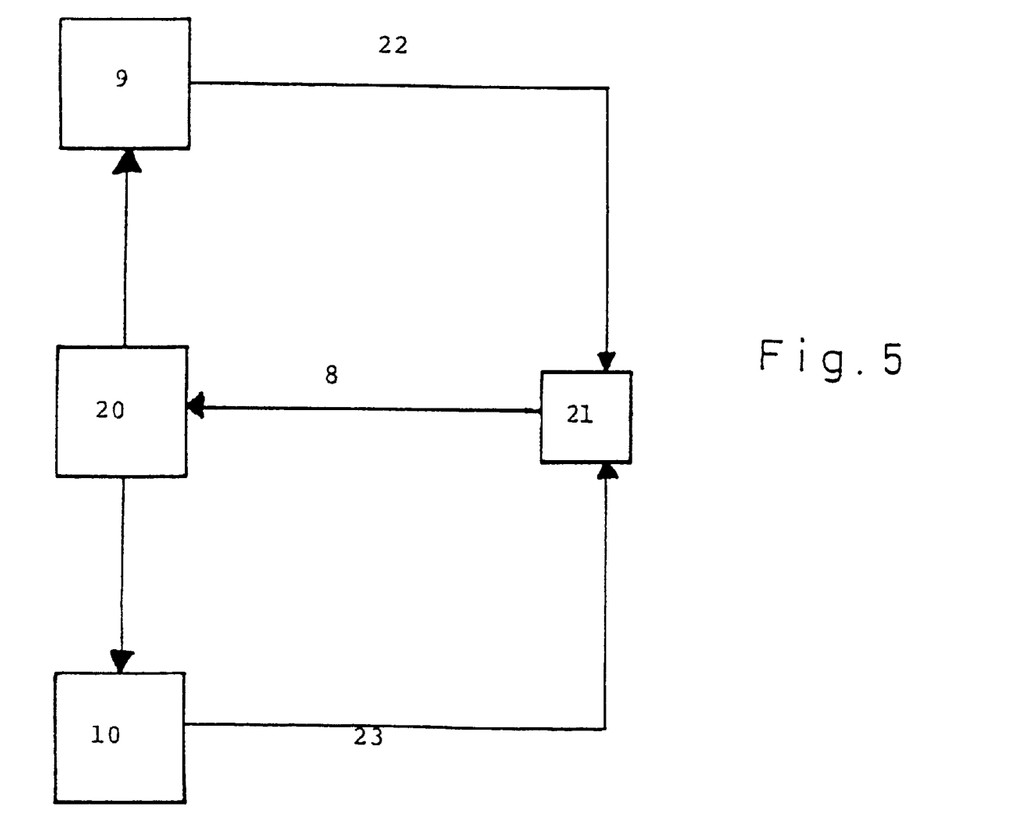
FIG. 5 diagrammatically shows a device according to the invention for inducing sedation (so-called closed loop arrangement).

FIG. 5 diagrammatically shows a device according to the invention with closed loop control for inducing sedation. Here, on the one hand, the effective xenon concentration in the blood is measured by measuring the inert gas in the exhaled air. On the other hand, other experimental data (for example acoustically induced potentials) are recorded on the patient. Both experimental results are used for controlling the perfusion pump.

The data pertaining to the xenon concentration in the exhaled air (xenon sensor/detector 9) and the acoustically induced potentials (recorder 10), recorded on a patient 20, are fed to the perfusion pump 21 via the data lines 22 and 23. The experimental data are processed (for example by means of a computer) and converted to the required infusion rate at which the xenon-containing preparation enters the patient via the line 8. In other words, the measured experimental data control the perfusion pump 21, which in turn determines the infusion rate. The device illustrated here is of course only a diagram and an actual device comprises indicators and regulators etc., as conventionally provided, for example in order also to allow manual intervention in the control. The supply line to the perfusion pump, and a storage container providing a xenon-laden preparation, are not shown.

Figure 6:
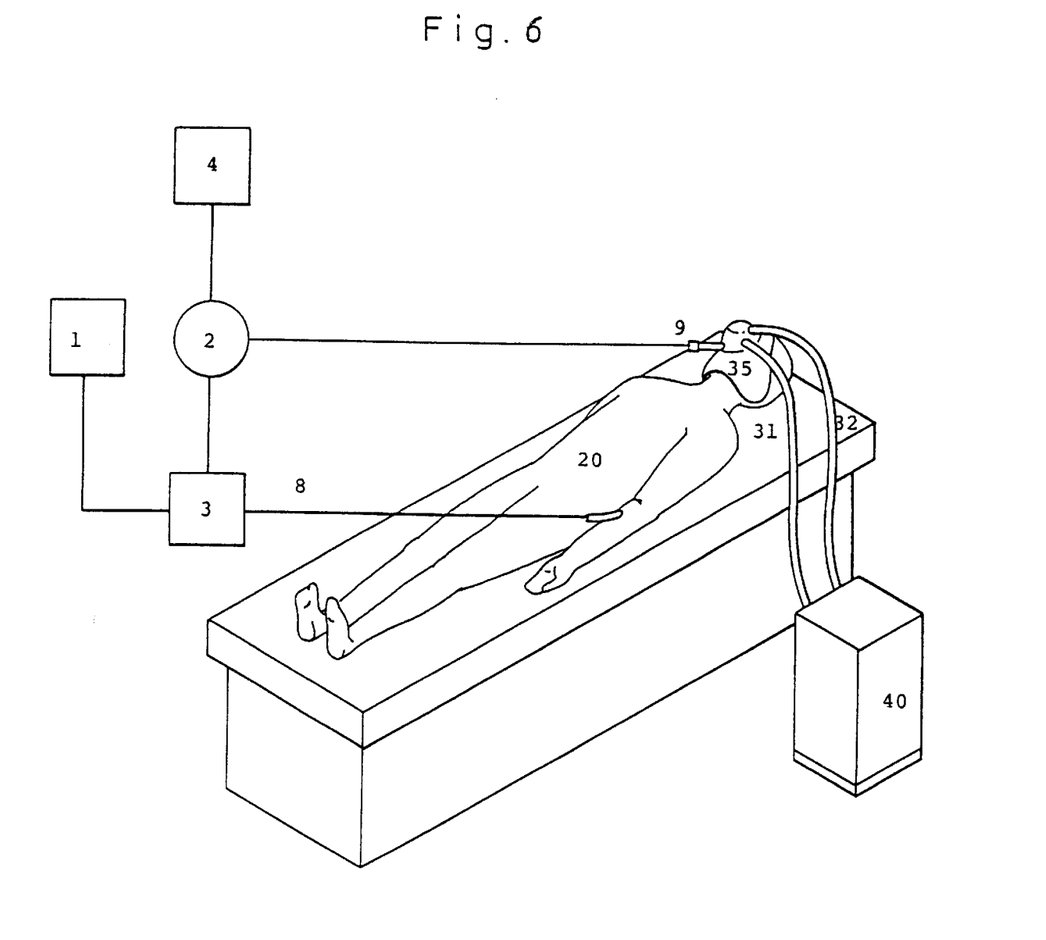
FIG. 6 shows a device according to the invention which is part of a device for carrying out anaesthesia with a gas, and which includes a means of measuring the inert gas in the exhaled air.

FIG. 6 diagrammatically shows how a device according to the invention can be incorporated into the general control of anaesthesia. This device comprises a storage container 1 for the preparation, the mixer 3, a xenon bottle 4 and a metering unit 2. The metering unit 2 is linked to a xenon detector 9, which measures the xenon concentration in the air at the end of exhalation and feeds an experimental value to the metering unit 2. The metering of the xenon into the liquid preparation is then controlled by the metering unit 2. The xenon-containing preparation then passes from the mixer 3 through the infusion tube 8 into the patient. The infusion rate can of course also be controlled via the xenon concentration in the exhaled air.

A control device 40 is also provided for supplying a gaseous or inhalation anaesthetic. This device comprises inlet and outlet tubes 31 and 32 for supplying and withdrawing the anaesthetic gas via the inhaling mask 35.

Experimental Section

Fatty emulsions

The commercially available Intralipid preparations (obtainable from Pharmacia & Upjohn GmbH, Erlangen) were used as fatty emulsions in the following Examples. These emulsions consist essentially of soya bean oil, 3-sn-phosphatidylcholine (from chicken egg yolk) and glycerol. An Intralipid® 10 fatty emulsion, for example, has the following composition:

| | |
|---|---|
| Soya bean oil | 100 g |
| (3-sn-Phosphatidyl)choline from | 6 g |
| chicken egg yolk | |
| Glycerol | 22.0 g |
| Water for injections ad | 1000 ml |
| Adjusted to pH | 8.0 with sodium hydroxide. |
| Energy value/l: | 4600 kJ (1100 kcal) |
| Osmolarity: | 260 mOsm/l |

An Intralipid 20 fatty emulsion, for example, has the following composition:

| | |
|---|---|
| Soya bean oil | 200 g |
| (3-sn-Phosphatidyl)choline from | 12 g |
| chicken egg yolk | |
| Glycerol | 22.0 g |
| Water for injections ad | 1000 ml |
| Adjusted to pH | 8.0 with sodium hydroxide. |
| Energy value/l: | 8400 kJ (2000 kcal) |
| Osmolarity: | 270 mOsm/l |

Loading of Perfluorocarbon Emulsion with Xenon

A series of perfluorocarbon emulsions were prepared or purchased and loaded with xenon. The activity of the preparations was verified on an animal model (rabbit). All the emulsions were used in the same way as the Intralipid preparations described above, i.e. the experimental animal was quickly anaesthetized by an injection in the ear (about 1 ml).

Each of the emulsions was placed in a beaker and loaded by having the xenon gas passed through it.

The following perfluorocarbon compounds were used: perfluorohexyloctane (1), perfluorodecalin (2), perflubron ($C_8F_{17}$) (3).

Emulsifiers, for example egg yolk lecithin (Lipoid E100 from Lipoid GmbH, Ludwigshafen), Pluronic PE6800 and Pluronic F68, were also used to prepare the emulsions.

It was established with all the emulsions that a perfluorocarbon emulsion of only 40% (weight/volume, i.e. weight of perfluorocarbon compound to volume of emulsion) could take up 1 to 4 ml of xenon per ml of emulsion.

Experimental Animal Studies

To demonstrate that it is possible according to the invention to control anaesthesia, in this case maintain anaesthesia, an experiment was performed on 24 pigs aged 14 to 16 weeks and weighing 36.4–43.6 kg. They were randomly divided into a total of 3 groups, which were anaesthetized. In all the groups the anaesthesia was induced intravenously with a bolus injection of pentobarbitone (8 mg/kg body weight) and buprenorphine (0.01 mg/kg body weight). In one group (comparative group) the anaesthesia was maintained by the intravenous administration of 2,6-diisopropylphenol (10 mg/1 ml emulsion). For maintenance of the anaesthesia, two groups of pigs (according to the invention), each containing four individuals, received an intravenous infusion of 1 ml/kg/h of a 10% by weight fatty emulsion according to the invention which had previously been saturated with xenon (about 0.3 ml of xenon per ml of emulsion). In group 2, 7.5 mg/kg body weight/h of 2,6-diisopropylphenol were additionally administered with the fatty emulsion.

The pigs underwent a surgical intervention (standard intervention: section of the left femoral artery) (identical in each group and for each experimental animal) and the adrenaline level, heart rate, arterial blood pressure and oxygen consumption were recorded. It was also established how much additional pentobarbitone needed to be administered in order to bring the analgesia and depth of anaesthesia to the required level in each group.

TABLE

| Group | Adrenaline pg/ml requirement | Heart rate [min$^{-1}$] | Arterial blood pressure [mm Hg] | VO$_2$ [ml/min] | Pentobarbitone mg/kg/min |
|---|---|---|---|---|---|
| Comparative | 60 | 115 | 110 | 410 | 0.25 |
| group | 134 | 120 | 105 | 391 | 0.36 |
|  | 112 | 105 | 115 | 427 | 0.31 |
|  | 85 | 98 | 101 | 386 | 0.42 |
| Group 1 | 38 | 112 | 112 | 341 | 0.09 |
|  | 21 | 106 | 100 | 367 | 0.04 |
|  | 16 | 95 | 104 | 348 | 0.11 |
|  | 30 | 112 | 118 | 334 | 0.15 |
| Group 2 | 10 | 88 | 100 | 325 | — |
|  | 23 | 100 | 85 | 346 | — |
|  | 14 | 94 | 93 | 331 | — |
|  | 8 | 104 | 87 | 354 | — |

The values indicated in the Table show that the xenon-containing preparation is superior to all the currently available intravenous anaesthetics, especially on account of the additional analgesic potency. Thus the pigs in group 1(10% by weight fatty emulsion saturated with xenon) show, by comparison (cf. comparative group), markedly less stress (adrenaline level), a lower oxygen requirement (VO$_2$) and a lower pentobarbitone requirement (i.e better anaesthesia). The difference relative to intravenous anaesthetics according to the state of the art is even more clearly apparent when the results in group 2 (fa10% fatty emulsion with 2,6-diisopropylphenol and enriched with xenon) are compared with the comparative group. This shows not only markedly reduced stress (adrenaline level). With a markedly reduced heart rate and lower arterial blood pressure, coupled with a lower oxygen requirement, it was possible to dispense with the administration of additional amounts of pentobarbitone.

This study shows that the desired aim, in this case to maintain the anaesthesia, can be achieved over the whole course of the anaesthesia.

The use of perfluorocarbon preparations was studied on another group (4 pigs of 31.4 to 39.8 kg body weight). A 40% perfluorocarbon emulsion with a xenon content of 2.1ml of xenon per ml of emulsion was used on this experimental group. For induction and intubation, the pigs recieved 20 ml of the emulsion intravenously over 20sec (corresponding to 1.34 ml xenon/kg body weight). After incubation and respiration, xenon was continuously infused intravenously over 30 min, the experimental animals thereby receiving a total of 75 ml of emulsion (corresponding to 10 ml xenon kg$^{-1}$ h$^{-1}$).

| Adrenaline [pg/ml] | Heart rate [min$^{-1}$] | Arterial blood pressure [mm Hg] | VO$_2$ [ml/min] |
|---|---|---|---|
| 8 | 90 | 101 | 301 |
| 6 | 87 | 96 | 320 |
| 10 | 94 | 98 | 308 |
| 5 | 100 | 106 | 316 |

The above Table indicates the experimental results for the adrenaline level, the heart rate, the artrial blood pressure and the oxygen consumption. The results show that, by increasing the xenon load and infusion rates (over 5 ml/kg/h), complete anaesthesia can effected using only the means according to the invention. Overall, it is even established that the oxygen requirement (VO$_2$) is lower and the anaesthesia adrenaline level and heart rate) is less stressed.

What is claimed is:

1. Device for controlled anaesthesia, analgesia and/or sedation, characterized in that the device comprises a container holding a liquid preparation which contains a lipophilic inert gas in an amount effective as an anaesthetic, analgesic or sedative, and means for the controlled intravenous administration of the liquid preparation to a patient.

2. Device according to claim 1 which comprises a perfuser for controlling the infusion rate of the liquid preparation.

3. Device according to claim 1 wherein the container is an infusion bag and has a tube and a regulator for controlling the infusion rate of the liquid preparation.

* * * * *